United States Patent
Lepi et al.

(10) Patent No.: US 12,202,083 B1
(45) Date of Patent: Jan. 21, 2025

(54) SYSTEMS AND METHODS FOR CONTROLLING WELDING SYSTEMS

(71) Applicant: Universal City Studios LLC, Universal City, FL (US)

(72) Inventors: Steven Michael Lepi, Satellite Beach, FL (US); Jordan Carlo Giovanetti, Orlando, FL (US)

(73) Assignee: Universal City Studios LLC, University City, CA (US)

( * ) Notice: Subject to any disclaimer, the term of this patent is extended or adjusted under 35 U.S.C. 154(b) by 0 days.

(21) Appl. No.: 18/240,834

(22) Filed: Aug. 31, 2023

Related U.S. Application Data

(63) Continuation of application No. 16/295,628, filed on Mar. 7, 2019, now abandoned.

(60) Provisional application No. 62/751,186, filed on Oct. 26, 2018.

(51) Int. Cl.
| | | |
|---|---|---|
| *G06F 30/23* | (2020.01) | |
| *B23K 9/095* | (2006.01) | |
| *G01N 33/207* | (2019.01) | |

(52) U.S. Cl.
CPC ......... *B23K 9/0953* (2013.01); *G01N 33/207* (2019.01)

(58) Field of Classification Search
CPC ...... B23K 9/0953; G06N 33/207; G06F 30/23
USPC .......................................................... 703/2
See application file for complete search history.

(56) References Cited

U.S. PATENT DOCUMENTS

| | | |
|---|---|---|
| 6,901,809 B2 | 6/2005 | Dong et al. |
| 7,752,917 B2 | 7/2010 | Tomioka |
| 2005/0071091 A1 | 3/2005 | Dong et al. |
| 2005/0171745 A1 | 8/2005 | Breitfeld et al. |
| 2010/0131256 A1 | 5/2010 | Hallquist |

(Continued)

FOREIGN PATENT DOCUMENTS

| | | |
|---|---|---|
| CN | 101882168 A | 11/2010 |
| CN | 105548005 A | 5/2016 |

(Continued)

OTHER PUBLICATIONS

Akhlaghi, Farshid Zamiri, "Fatigue Life Assessment of Welded Bridge Details Using Structural Hot Spot Stress Method", Jan. 1, 2009, pp. 1-122, Sweden 2009.

(Continued)

*Primary Examiner* — Andre Pierre Louis
(74) *Attorney, Agent, or Firm* — Fletcher Yoder P.C.

(57) ABSTRACT

Systems and methods described herein are configured to control welding systems, for example, controlling welding process variables based at least in part on nominal stresses estimated using finite element (FE) algorithms. The systems and methods described herein may be utilized to identify nominal stress in welded structures and components to enable adjustment of welding process variables for the manufacture of subsequent welded structures and components, for example, performed by the same welding system. The systems and methods described herein also allow readily available FE stress results to be utilized in a consistent manner, as well as providing user feedback regarding the accuracy of the nominal stress approximations. Furthermore, the systems and methods described herein are generally faster and less error prone than conventional techniques, and are relatively insensitive to mesh density of the FE stress calculations.

20 Claims, 5 Drawing Sheets

(56) References Cited

U.S. PATENT DOCUMENTS

| | | | |
|---|---|---|---|
| 2012/0259593 A1* | 10/2012 | El-Zein | G06F 30/23 |
| | | | 703/1 |
| 2014/0207316 A1* | 7/2014 | Kolambekar | B61L 15/0027 |
| | | | 701/19 |
| 2017/0191915 A1 | 7/2017 | Shirakami et al. | |
| 2019/0054573 A1 | 2/2019 | Dong et al. | |

FOREIGN PATENT DOCUMENTS

| | | | |
|---|---|---|---|
| CN | 106339541 A | 1/2017 | |
| JP | 2003149130 A | 5/2003 | |
| JP | 2015090673 A | 5/2015 | |

OTHER PUBLICATIONS

Aygul, Mustafa; "Fatigue Analysis of Welded Structures Using the Finite Element Method," Department of Civil and Environmental Engineering Division of Structural Engineering, Steel and Timber Structures, Chalmers University of Technology, Gothenburg, Sweden, 2012, pp. 1-56.

Chakraborti et al.; "Confidence Interval Estimation of a Normal Percentile," The American Statistician, Feb. 2007, pp. 1-6 (Year: 2007).

"Eurocode 3: Design of Steel Structures—Part 1-9: Fatigue," The European Union Edict of Government, European Committee for Standardization, May 2005, pp. 1-37.

Hobbacher, A.; "Recommendations for Fatigue Design of Welded Joints and Components," International Institute of Welding, Oct. 2008, pp. 1-149.

Lazzarin et al., "Rapid calculations of notch stress intensity factors based on averaged strain energy density from coarse meshes: Theoretical bases and applications," International Journal of Fatigue, 2010, pp. 1559-1567, vol. 32, Issue 10.

Lee, Jae-Myung et al.; "Comparison of hot spot stress evaluation methods for welded structures," International Journal of Naval Architecture and Ocean Engineering, Society of Naval Architects of Korea, 2010, pp. 2:200-2:210.

Liu, Yuchang; "Effects of Mesh Density on Finite Element Analysis," SAE International 2013-01-1375, Apr. 2013, 8 pgs. (Year: 2013).

Olsen, Robin Krogh, et al.; "Non-Linear Assessment on Non Full-Strength Welded Joints", Jun. 1, 2018, pp. 1-135.

Sledziewski, Krzysztof; "Fatigue Assessment for Selected Connections of Structural Steel Bridge Components Using the Finite Element Method," AIP Conference Proceedings 1922, Jan. 8, 2018, 10 pgs. (Year: 2018).

Wei, et al.; "Fatigue Assessment and stress analysis of cope-hole details in welded joints of steel truss bridge," International Journal of Fatigue 100, 2017, pp. 136-147. (Year: 2017).

IN Office Action for India Application No. 202117018856 mailed Jan. 23, 2023.

PCT/US2019/053975 International Search Report and Written Opinion Jan. 7, 2020.

JP Office Action for Japanese Application No. 2021-521797 mailed Nov. 1, 2023.

CN Office Action for Chinese Application No. 201980070854.8 mailed Mar. 18, 2024.

AE Office Action for United Arab Emirates Application No. P6000641/2021 mailed Oct. 23, 2024.

* cited by examiner

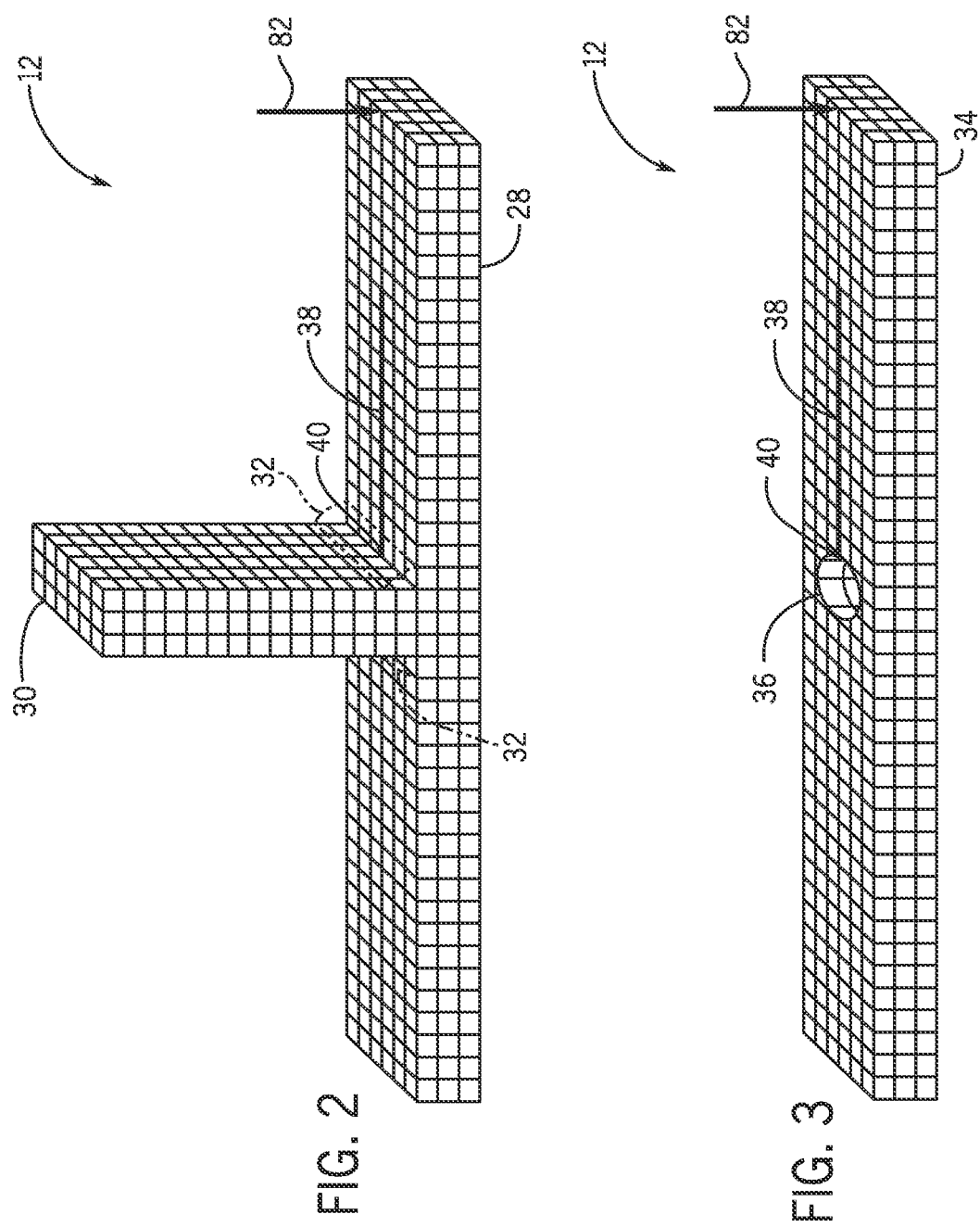

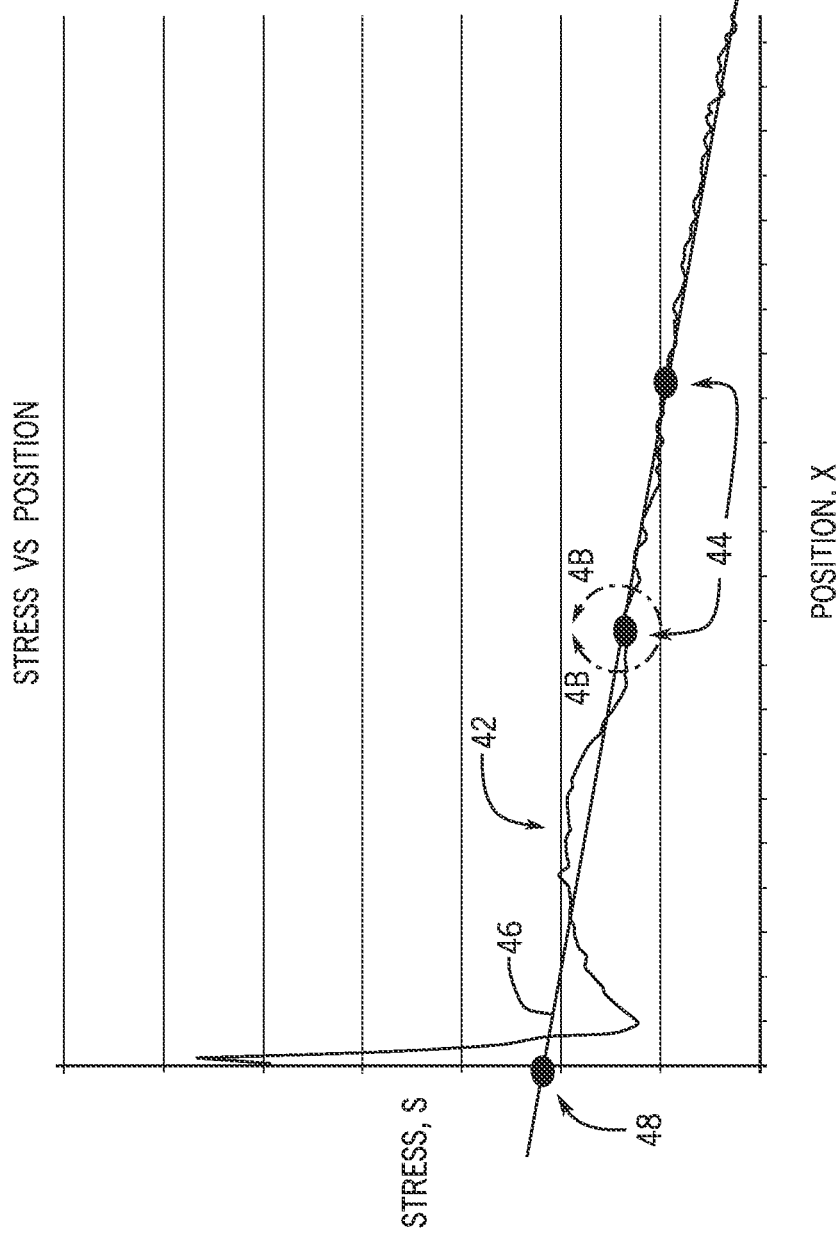

SYSTEMS AND METHODS FOR CONTROLLING WELDING SYSTEMS

CROSS REFERENCE TO RELATED APPLICATION

This application is a continuation of U.S. patent application Ser. No. 16/295,628, filed Mar. 7, 2019, which claims priority to and the benefit of U.S. Provisional Application No. 62/751,186, filed Oct. 26, 2018, which are incorporated herein by reference in their entirety for all purposes.

BACKGROUND

The present disclosure relates generally to systems and methods for controlling welding systems. More specifically, embodiments of the present disclosure related to controlling welding process variables based at least in part on nominal stresses estimated using finite element (FE) algorithms.

This section is intended to introduce the reader to various aspects of art that may be related to various aspects of the present disclosure, which are described below. This discussion is believed to be helpful in providing the reader with background information to facilitate a better understanding of the various aspects of the present disclosure. Accordingly, it should be understood that these statements are to be read in this light, and not as admissions of prior art.

Weld fatigue prediction standards typically allow the use of nominal stress metrics. However, stress in welded structures is often calculated using FE calculation methods, which do not directly compute nominal stress. Rather, nominal stress typically has to be estimated based on, for example, separate calculations. For example, certain conventional methods of approximating nominal stress include utilizing FE-generated forces and moments in conjunction with hand calculations, while others utilize a coarse FE mesh to minimize local stress raising effects of a weld joint root, while yet others extrapolate FE-calculated stresses based upon certain geometric parameters, such as plate thickness, which may not be easily identifiable in practical applications. In general, these conventional methods tend to be relatively time consuming, error prone, or in the case of utilizing a coarse FE mesh approach, somewhat arbitrary or tedious.

SUMMARY

Certain embodiments commensurate in scope with the originally claimed subject matter are summarized below. These embodiments are not intended to limit the scope of the disclosure, but rather these embodiments are intended only to provide a brief summary of certain disclosed embodiments. Indeed, the present disclosure may encompass a variety of forms that may be similar to or different from the embodiments set forth below.

The embodiments described herein relate to a welding control system that includes memory media storing processor-executable instructions comprising finite element (FE) analysis algorithms configured to calculate stresses of a welded structural component and control a welding process of a welding system based at least in part on the calculated stresses, and one or more processors configured to execute the FE analysis algorithms. The FE analysis algorithms, when executed by the one or more processors, cause the welding control system to calculate the stresses at a plurality of points from a base point along a base line of the welded structural component; spline-fit the calculated stresses versus the plurality of points from the base point along the base line of the welded structural component; identify two or more points of the plurality of points by evaluating second derivatives of the spline-fitted calculated stresses for adjacent points of the plurality of points, wherein identifying the two or more points of the plurality of points comprises identifying each point of the two or more points of the plurality of points by identifying a subset of points adjacent the respective point, wherein a second derivative of each of the subset of points is within a threshold percentage of each other, wherein the threshold percentage is 5%, and wherein the subset of points comprises five points; estimate a nominal stress at the base point by extrapolating calculated stresses of the identified two or more points of the plurality of points to the base point; and output a control signal to adjust a welding process variable of the welding system for the manufacture of a subsequent welded structural component by the welding system based at least in part on the estimated nominal stress at the base point.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIG. 2 is a perspective view of a welded structural component for which nominal stresses may be estimated by the control system of FIG. 1, in accordance with embodiments of the present disclosure;

FIG. 3 is a perspective view of a non-welded structural component for which nominal stresses may be estimated by the control system of FIG. 1, in accordance with embodiments of the present disclosure;

FIG. 4A illustrates a graph of stress values at various points along a base line of a structural component, such as the structural components illustrated in FIGS. 2 and 3, in accordance with embodiments of the present disclosure;

FIG. 4B illustrates a zoomed-in view of the graph illustrated in FIG. 4A, in accordance with embodiments of the present disclosure;

DETAILED DESCRIPTION

Figure 1:
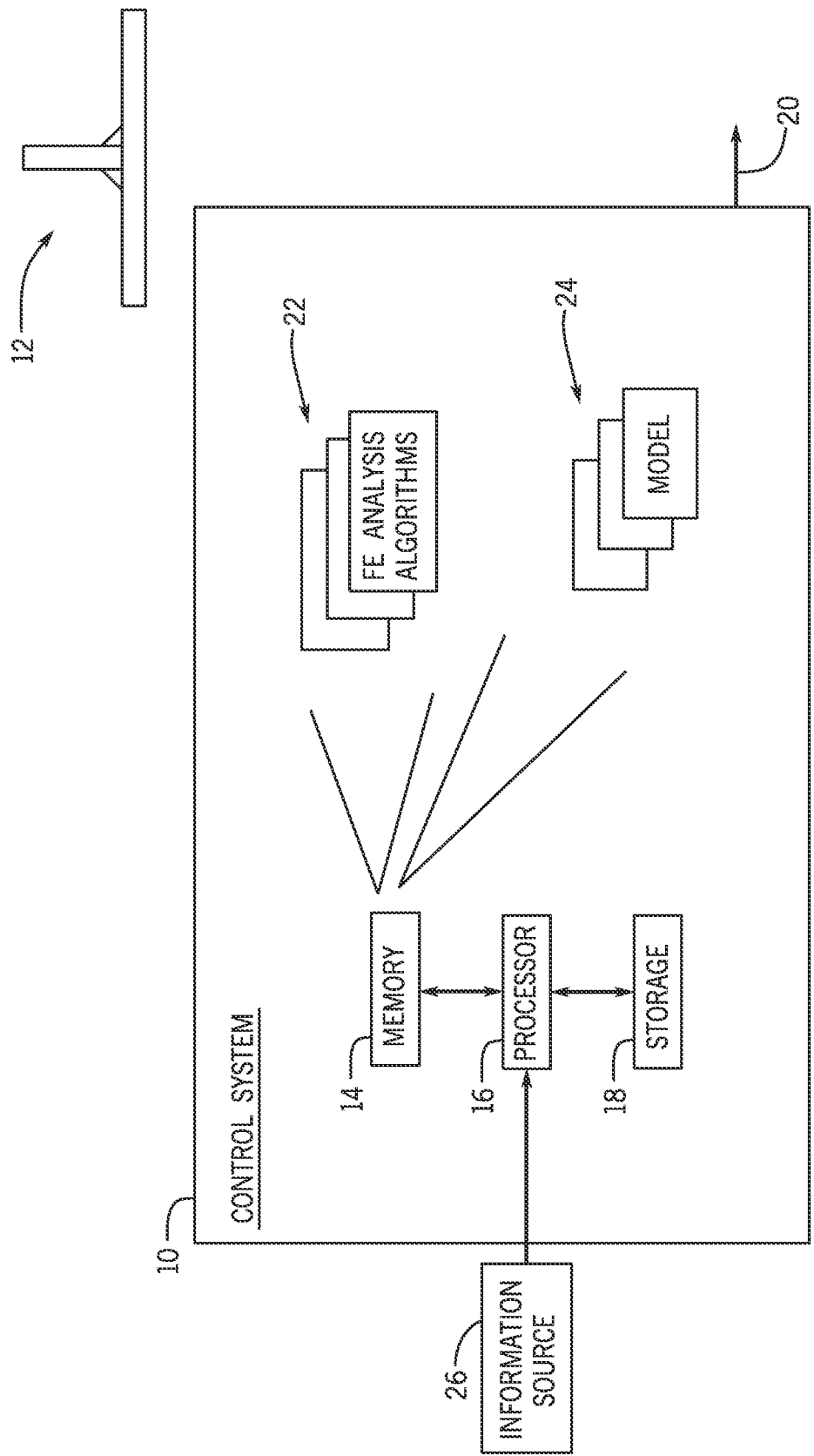
FIG. 1 illustrates an embodiment of a control system configured to estimate nominal stresses in a structural component, in accordance with embodiments of the present disclosure.

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

The embodiments described herein include systems and methods for estimating nominal stress using FE stress calculations, without hand calculations, specific mesh density requirements, identifying specific geometric parameters, such as plate thickness, or finite element representations of the weld bead. The systems and methods described herein may be utilized to identify nominal stress in the parent material of welded structures and components, and also in non-welded components that have stress raisers due to other causes. The systems and methods described herein also allow readily available FE stress results to be utilized in a consistent manner, as well as providing user feedback regarding the accuracy of the nominal stress approximations. Furthermore, the systems and methods described herein are generally faster and less error prone than the conventional techniques described herein, and are relatively insensitive to mesh density of the FE stress calculations. As described herein, the term "nominal stress" is intended to exclude certain stress concentration effects. Hence, as described herein, nominal stress along any one base line is assumed to exhibit linear behavior some distance from a base point, such as a weld joint root or stress raiser, where nonlinear effects from the base point no longer dominate. In certain embodiments, multiple base lines may be employed, and nominal stress is assumed to exhibit linear behavior along each base line. In addition, in certain embodiments, a linearity check may be performed to verify that stress exhibits linear characteristics some distance from a base point.

FIG. 1 illustrates an embodiment of a welding control system 10 configured to estimate nominal stresses in a structural component 12, in accordance with embodiments of the present disclosure. As illustrated, in certain embodiments, the welding control system 10 includes a memory device 14 (e.g., a non-transitory computer readable medium) and a processor 16 configured to execute computer readable instructions stored on the memory device 14. In certain embodiments, the processor 16 may include multiple processors, one or more general-purpose microprocessors, one or more special-purpose microprocessors, and/or one or more application specific integrated circuits (ASICs), or some combination thereof. For example, in certain embodiments, the processor 16 may include one or more reduced instruction set (RISC) processors, advanced RISC machine (ARM) processors, performance optimization with enhanced RISC (PowerPC) processors, field-programmable gate array (FPGA) integrated circuits, graphics processing units (GPUs), or any other suitable processing device.

In certain embodiments, the memory device 14 may include a volatile memory, such as random access memory (RAM), nonvolatile memory, such as read-only memory (ROM), flash memory, or any combination thereof. The memory device 14 may store a variety of information that may be used for various purposes. For example, in certain embodiments, the memory device 14 may store processor-executable instructions (e.g., firmware or software) for the processor 16 to execute, such as instructions for estimating nominal stresses in structural components 12. In addition, in certain embodiments, the processor 16 may store information relating to the nominal stresses in one or more storage device(s) 18. For example, in certain embodiments, the one or more storage device(s) 18 (e.g., nonvolatile storage) may include ROM, flash memory, a hard drive, or any other suitable optical, magnetic, or solid-state storage medium, or a combination thereof. In addition, in certain embodiments, the processor 16 may be configured to output a control signal 20 to an associated welding system, which may be usable for the control of the manufacture of one or more subsequent structural components 12.

As described in greater detail herein, the processor 16 may execute instructions stored in the memory device 14 relating to using FE analysis algorithms 22 to calculate stresses at a plurality of points of the structural component 12. To that end, in certain embodiments, the processor 16 may utilize one or more model(s) 24 of the structural component 12, which may for example be stored in the memory device 14 or the one or more storage device(s) 18 and/or may be received from an information source 26 external to the welding control system 10. In certain embodiments, once the processor 16 has calculated the stresses at the plurality of points of the structural component 12 using the FE analysis algorithms 22, the processor 16 may identify two or more points of the plurality of points along a base line (e.g., in a linear direction) of the structural component 12 that have respective calculated stresses that are unaffected by stress raising effects at a base point (e.g., a weld joint root of a welded structural component 12 where the welded members are closest to each other, a stress raiser of a non-welded structural component 12, or some other point at which a stress raising effect may occur) of the structural component 12. As described in greater detail herein, in certain embodiments, the processor 16 may identify the two or more points along a base line of the structural component 12 as having respective calculated stresses that are unaffected by stress raising effects at a base point of the structural component 12 by, for example, evaluating second derivatives of calculated stress for adjacent points of the plurality of points of the structural component 12.

It should be noted that, in certain embodiments, weld bead geometry need not be included in the FE idealization using the FE analysis algorithms 22. Rather, in certain embodiments, weld joints may be idealized using coincident nodes, or bonded contact with no penetration. In addition, in certain embodiments, the instructions executed by the processor 16 may assume that stresses are due only to external forces and moments; however, in other embodiments, more complex stress analysis may be performed. It is also noted that, in certain embodiments, the instructions executed by the processor 16 may assume that stresses, at a location sufficiently distant from a weld joint root or other stress raiser, will decrease linearly with distance from the weld joint root, stress raiser, or other point at which a stress raising effect may occur; however, again, more complex stress analysis may be performed in other embodiments. In certain embodiments, the processor 16 may perform a linearity check to verify that stresses do, in fact, exhibit linear characteristics some distance from a base point.

In certain embodiments, once the processor 16 has identified the two or more points along the base line of the structural component 12, which have a respective calculated stress that is unaffected by stress raising effects at a base point of the structural component 12, the processor 16 may estimate a nominal stress at the base point of the structural component 12 by, for example, extrapolating calculated stresses at the identified two or more points back to the base point of the structural component 12. As such, as described in greater detail herein, the processor 16 may estimate the nominal stress at the base point of the structural component 12 with little sensitivity to a mesh density used in the FE analysis algorithms 22. Rather, the embodiments described herein use relatively simple extrapolation of calculated stresses along the base line (e.g., in any linear direction) of the structural component 12 based on the two or more points along the base line that are determined by the processor 16 to have a respective calculated stress that is unaffected by stress raising effects at the base point of the structural component 12.

The embodiments described herein may be equally usable for estimating nominal stresses in welded structural components 12 as well as non-welded structural components 12. For example, FIG. 2 is a perspective view of a welded structural component 12 for which nominal stresses may be estimated by the welding control system 10 of FIG. 1, in accordance with embodiments of the present disclosure. As illustrated in FIG. 2, the welded structural component 12 includes a base member 28 and a secondary member 30 welded to the base member 28 via fillet welds 32 on opposite sides of the secondary member 30. However, it will be appreciated that the embodiments described herein may be equally usable for estimating nominal stresses at other types of welds. As described herein, in certain embodiments, the weld joint root (e.g., the intersections between the base member 28 and the secondary member 30 for the weld 32) may be considered base points 40 at which nominal stresses may be estimated by the welding control system 10 of FIG. 1.

In contrast, FIG. 3 is a perspective view of a non-welded structural component 12 for which nominal stresses may be estimated by the welding control system 10 of FIG. 1, in accordance with embodiments of the present disclosure. As illustrated in FIG. 3, the non-welded structural component 12 includes a single (e.g., solid) structural member 34. However, as illustrated, the solid structural member 34 of the non-welded structural component 12 of FIG. 3 includes one or more stress raisers 36 (e.g., a hole or other structural feature) at which nominal stresses may be different due to the structural nature of the one or more stress raisers 36. As described herein, in certain embodiments, the one or more stress raisers 36 of the non-welded structural component 12 illustrated in FIG. 3 may be considered base points 40 at which nominal stresses may be estimated by the welding control system 10 of FIG. 1.

As illustrated in FIGS. 2 and 3, regardless of the specific type of base point (e.g., welds 32 or stress raisers 36), the structural component 12 may be analyzed by the welding control system 10 of FIG. 1 (e.g., by the processor 16 executing the FE analysis algorithms 22) as having a certain mesh density to calculate the stresses at certain points (e.g., intersections of the mesh) of the structural component 12. However, as described in greater detail herein, the embodiments of the present disclosure are capable of estimating nominal stresses at the base points 40 of structural components 12 without significant influence from the particular mesh density used by the FE analysis algorithms 22. Specifically, as also illustrated in FIGS. 2 and 3, in certain embodiments, once the stresses at the plurality of points of the structural component 12 are calculated using the FE analysis algorithms 22, the processor 16 may consider the FE-calculated stress for each of the individual points along a straight base line 38 (e.g., in a linear direction) that extends from a base point 40 (e.g., at the weld joint root associated with the weld 32 or the stress raiser 36) along the base line 38 to a distal point some linear distance away from the base point 40.

As described in greater detail herein, the embodiments of the present disclosure are capable of estimating nominal stresses at base points 40 of structural components 12 regardless of specific geometric features of the structural components 12. Rather, by estimating nominal stresses at base points 40 of structural components 12 by considering FE-calculated stresses along base lines 38 extending from the base points 40, the embodiments described herein obviate the need to consider specific geometric features of the structural components 12 by instead identifying points along the base lines 38 that have calculated stresses that are determined to be unaffected by stress raising effects at the base points 40.

To further illustrate how the welding control system 10 of FIG. 1 estimates nominal stresses at the base points 40 of structural components 12, FIG. 4A illustrates a graph of stress values at various points along a base line 38 of a structural component 12, such as the structural components 12 illustrated in FIGS. 2 and 3, in accordance with embodiments of the present disclosure. In particular, FIG. 4A illustrates a series 42 of FE-calculated stress values (e.g., as determined by the processor 16 of the welding control system 10 using FE analysis algorithms 22) at various positions along a base line 38 of a structural component 12. It will be appreciated that the 0 value for the Position axis is analogous to the base point 40 (e.g., at a weld joint root associated with a weld 32 of the welded structural component 12 illustrated in FIG. 2 or a stress raiser 36 of the non-welded structural component 12 illustrated in FIG. 3) of the structural component 12.

As illustrated in FIG. 4A, the processor 16 of the welding control system 10 may identify two or more points 44 of the series 42 of FE-calculated stress values where the FE-calculated stress values are unaffected by stress raising effects at the base point 40 of the structural component 12. As illustrated by line 46 in FIG. 4A, once the processor 16 has identified the two or more points 44 that have FE-calculated stress values that are unaffected by stress raising effects at the base point 40 of the structural component 12, the processor 16 may extrapolate the FE-calculated stress values of the two or more points 44 back to the 0 value of the Position axis, which again corresponds to the base point 40 of the structural component 12. The processor 16 of the welding control system 10 then determines that the intersection 48 of the extrapolation line 46 with the Stress axis is the estimated nominal stress value of the base point 40 of the structural component 12.

In certain embodiments, in order to identify the two or more points 44 that have FE-calculated stress values that are unaffected by stress raising effects at the base point 40 of the structural component 12, the processor 16 of the welding control system 10 may compare rates of change of slopes (e.g., a second derivative) of the series 42 of FE-calculated stress values for adjacent points along the Position axis (e.g., which, again, correspond to points along the base line 38 of the structural component 12). It will be appreciated that the slopes of calculated stress at any given point along the Position axis will be equal to $\delta s/\delta x$ at that particular point, and that the rates of change of slopes (e.g., the second derivative) of calculated stress at any given point along the Position axis will be equal to $\delta^2 s/\delta x^2$, where s is equal to the calculated stress (i.e., along the Stress axis), and x is equal to the distance from the base point 40 along the base line 38 of the structural component 12 (i.e., along the Position axis).

To further illustrate how the welding control system 10 of FIG. 1 identifies the two or more points 44 that have FE-calculated stress values that are unaffected by stress raising effects at the base point 40 of the structural component 12, FIG. 4B illustrates a zoomed-in view of the graph illustrated in FIG. 4A, in accordance with embodiments of the present disclosure. In particular, FIG. 4B illustrates twelve distinct points 50, 52, 54, 56, 58, 60, 62, 64, 66, 68, 70, and 72 of the series 42 of FE-calculated stress values.

In certain embodiments, the processor 16 of the welding control system 10 may identify point 62 as one of the two or more points 44 that have FE-calculated stress values that are unaffected by stress raising effects at the base point 40 of the structural component 12. In particular, in certain embodiments, the processor 16 of the welding control system 10 may make this determination based on the fact that a given number of points adjacent point 62 have a second derivative that does not deviate from the second derivative at point 62 by more than a threshold percentage. For example, in certain embodiments, the processor 16 of the welding control system 10 may determine that points 58, 60, 62, 64, and 66 all have second derivatives that do not deviate by more than 10%, more than 5%, more than 2%, more than 1%, or even less, from each other. As such, the processor 16 of the welding control system 10 may determine that point 62 is one of the two or more points 44 that have FE-calculated stress values that are unaffected by stress raising effects at the base point 40 of the structural component 12. It will be appreciated that, in such embodiments, the processor 16 of the welding control system 10 identifies point 62 as one of the two or more points 44 that have FE-calculated stress values that are unaffected by stress raising effects at the base point 40 of the structural component 12 by analyzing a subset of points adjacent point 62 (e.g., point 62 itself, along with two points on either side of point 62) such that five points are included in the subset of points. However, it will be appreciated that, in other embodiments, any numbers of points may be used for the subset of points, such as three points, seven points, nine points, or even more.

Figure 5:
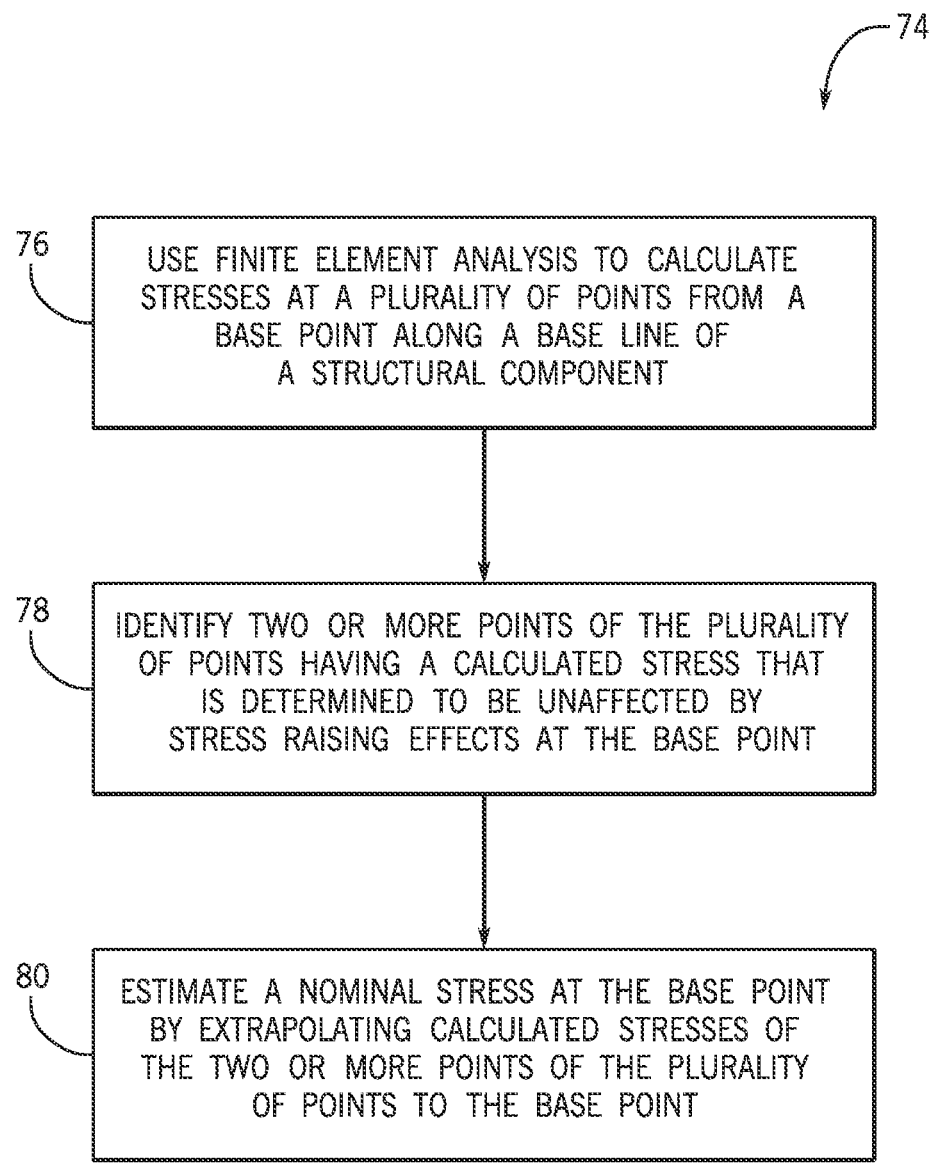
FIG. 5 is a flow diagram of a method of estimating nominal stress in a structural component, which may be executed by the control system of FIG. 1, in accordance with embodiments of the present disclosure.

FIG. 5 is a flow diagram of a method 74 of estimating nominal stress in a structural component 12, which may be executed by the welding control system 10 of FIG. 1, in accordance with embodiments of the present disclosure. In particular, as described in greater detail herein, the processor 16 of the welding control system 10 of FIG. 1 may be configured to execute instructions stored in the memory device 14 of the welding control system 10, wherein the instructions are configured to carry out the method 74 illustrated in FIG. 5. As illustrated in block 76 of FIG. 5, in certain embodiments, the instructions may include instructions for using FE analysis algorithms 22 to calculate stresses at a plurality of points extending from a base point 40 (e.g., a weld joint root associated with a weld 32 of a welded structural component 12, as illustrated in FIG. 2, or a stress raiser 36 of a non-welded structural component 12, as illustrated in FIG. 3) along a base line 38 of a structural component 12. For example, in certain embodiments, the processor 16 of the welding control system 10 may be configured to execute FE analysis algorithms 22 based on one or more model(s) 24 of the structural component 12 to calculate the stresses at the plurality of points along the base line 38 of the structural component 12.

In addition, as illustrated in block 78 of FIG. 5, in certain embodiments, the instructions may include instructions for identifying two or more points 44 of the plurality of points along the base line 38 of the structural component 12 that have an FE-calculated stress value that is determined to be unaffected by stress raising effects at the base point 40 of the structural component 12. For example, in certain embodiments, the processor 16 of the welding control system 10 may be configured to identify the two or more points 44 that have an FE-calculated stress value that is determined to be unaffected by stress raising effects at the base point 40 of the structural component 12 by comparing second derivatives of FE-calculated stress value for adjacent points, for example, as described in greater detail with respect to FIG. 4B.

In addition, as illustrated in block 80 of FIG. 5, in certain embodiments, the instructions may include instructions for estimating a nominal stress at the base point 40 of the structural component 12 by extrapolating FE-calculated stress values of the identified two or more points 44 of the plurality of points back to the base point 40 of the structural component 12, for example, as described in greater detail with respect to FIG. 4A. As described herein, in certain embodiments, the welding control system 10 may use the estimated nominal stress at the base point 40 of the structural component 12, for example, to output a control signal (e.g., control signal 20, as illustrated in FIG. 1), which may be usable for control of the manufacture of one or more subsequent structural components 12 by an associated welding system. For example, in certain embodiments, if the processor 16 of the welding control system 10 estimates the nominal stress at the weld joint root associated with the weld 32 of the welded structural component 12 as being higher (or lower) than anticipated, the processor 16 may output a control signal (e.g., control signal 20, as illustrated in FIG. 1) that is usable to adjust a dimension of a welded structural component 12, adjust a welding process variable of an associated welding system, or make any other adjustment, for the manufacture of a subsequent welded structural component 12, for example, by the same welding system.

In certain embodiments, the modeling and simulation performed by the welding control system 10 may begin by creating a base line 38 (or multiple base lines 38) perpendicular to the welded area of interest. For example, as illustrated in FIG. 2, the welded area of interest may include the weld joint root (e.g., at an intersection of the members 28 30) associated with the weld 32, and the base line 38 perpendicular to the welded area of interest may include the straight base line 38 that extends from the base point 40. In general, the base line 38 is located directly on the member of interest (i.e., the member that will fail first, for example, the base member 28 in the embodiment illustrated in FIG. 2). Then, the welding control system 10 may create a simulation study and apply materials for the members 28, 30, one or more loads 82 on the members 28, 30, and boundary conditions of the members 28, 30. Then, the welding control system 10 may model component contact reflective of the weld 32, for example, bonded contact on edges of the welded member 28, 30, and no penetration contact between the members 28, 30. Then, the welding control system 10 may mesh the structural component 12. In certain embodiments, mesh control (e.g., in conjunction with a fine mesh option) may be applied by the welding control system 10 in the welded area of interest. Then, the welding control system 10 may execute the study and ensure, for example, that the structural component 12 is reacting to loads 82 properly by considering the displacement deformed results to ensure the structural component 12 is properly constrained. Then, the welding control system 10 may examine the von Mises (or other) stress results by probing the base line 38. In certain embodiments, the welding control system 10 may ensure that the first nodal value being probed resides upon the weld joint root. It is noted that when metrics other than von Mises stress are used, in certain embodiments, the welding control system 10 may ensure that the chosen metric references a coordinate system that is oriented with respect to the base line 38. Then, the welding control system 10 may extract the stress and position values along the base line 38.

Figure 6:
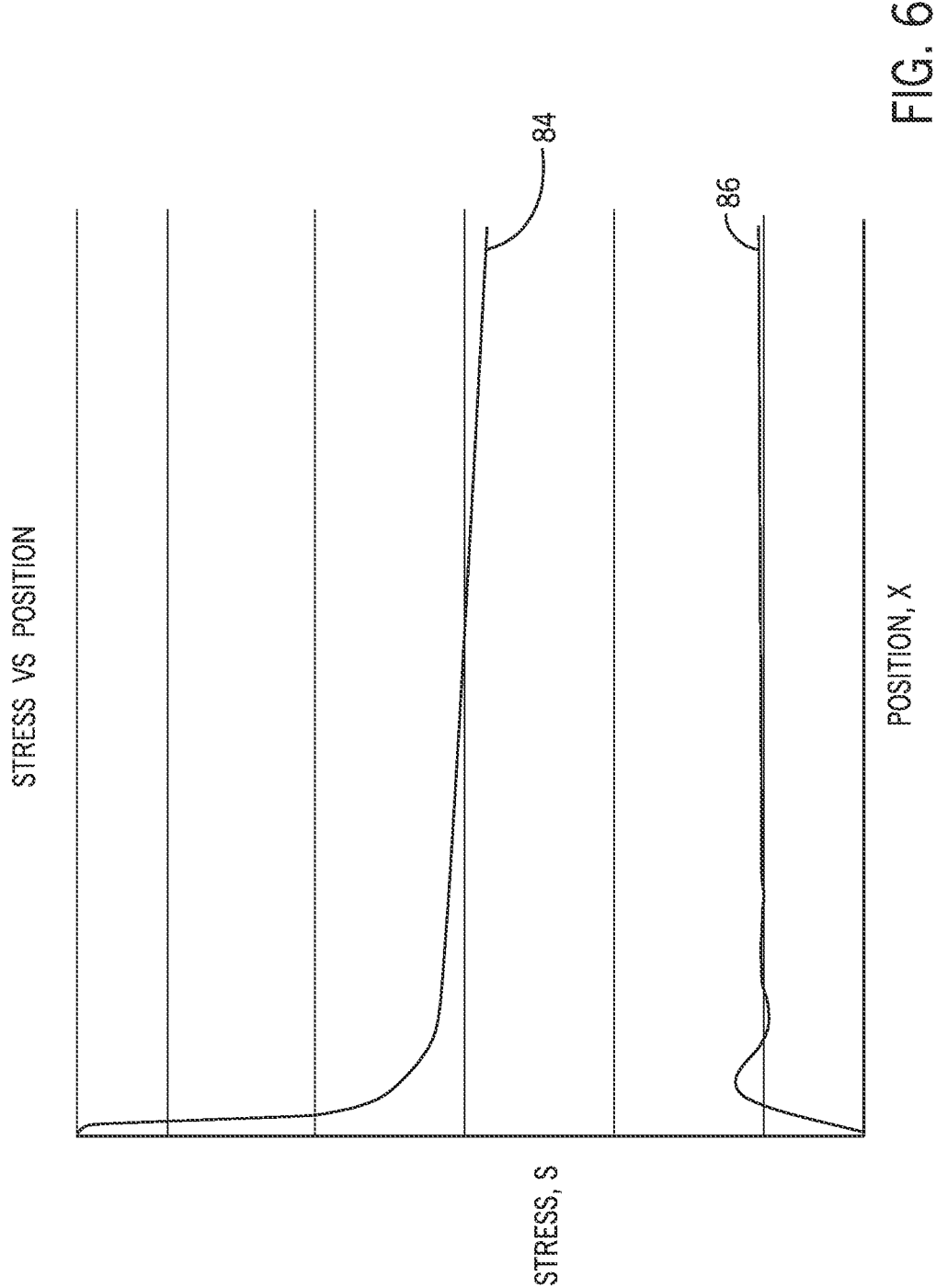
FIG. 6 illustrates a graph of spline-fit stress and a filtered second derivative of stress at various points along a base line of a structural component, such as the structural components illustrated in FIGS. 2 and 3, in accordance with embodiments of the present disclosure.

Once the stress and position values are extracted by the welding control system 10, data manipulation performed by the welding control system 10 may begin with evenly spacing the position data, if it is not already evenly spaced. Then, the welding control system 10 may spline-fit the stress versus position data (e.g., with a 4th order spline, in certain embodiments). Then, the welding control system 10 may double differentiate the stress with respect to position (e.g., using a central difference method, in certain embodiments). Then, the welding control system 10 may filter the double differentiated data (e.g., using a Butterworth filter with a low pass, forward and backward method having a cutoff frequency of 0.07 and a stop frequency of unity, in certain embodiments), and plot both the spline-fit stress versus position data, and the filtered second derivative of stress versus position data. FIG. 6 illustrates a graph of the spline-fit stress 84 and the filtered second derivative of stress 86 at various points along a base line 38 of a structural component 12, such as the structural components 12 illustrated in FIGS. 2 and 3, in accordance with embodiments of the present disclosure. Then, the welding control system 10 may calculate an absolute difference of the filtered second derivative of stress 86 between each value of x (e.g., to two decimal places, in certain embodiments).

Then, the welding control system 10 may identify a first instance along the Position (i.e., x) axis where a certain number of consecutive points (e.g., three consecutive points, five consecutive points, seven consecutive points, nine consecutive points, or even more, in certain embodiments) have an absolute difference of the filtered second derivative of stress 86 between adjacent points that is less than a given threshold percentage (e.g., less than 10%, less than 5%, less than 2%, less than 1%, or even less, in certain embodiments). It will be appreciated that this first identified instance is the first of the identified points 44 illustrated in FIG. 4A. In certain embodiments, the welding control system 10 may identify a second point 44 at some set distance from the first identified point 44 (e.g., 1.5 times the position value along the Position axis, in certain embodiments), and the two identified points 44 may be determined to have respective calculated stresses that are unaffected by the stress raising effect at the base point 40 of the structural component 12.

In certain embodiments, if the welding control system 10 determines that the calculated stress associated with the second identified point 44 is greater than a given threshold (e.g., greater than 10%, greater than 5%, greater than 2%, greater than 1%, or even less, in certain embodiments) of the calculated stress associated with the first identified point 44, the welding control system 10 may re-run the analysis on only the data prior to and including the first identified point 44 along the Position axis. In other words, the welding control system 10 may treat the data beyond the first identified point 44 as presenting a nonlinearity that should be excluded from analysis. Otherwise, the welding control system 10 may use the two (or more) identified points 44 (as well as all data in between these points 44, in certain embodiments) to perform the linear regression illustrated in FIG. 4A. In certain embodiments, the welding control system 10 may ensure that the R-squared value of the linear regression is greater than a given threshold (e.g., greater than 0.7, greater than 0.75, greater than 0.8, greater than 0.85, greater than 0.9, or even greater, in certain embodiments). As described in greater detail with respect to FIG. 4A, the y-intercept value of the linear regression (i.e., the value of linearized stress at the Position value of 0) represents the estimated nominal stress at the base point 40.

As described herein, embodiments of the present disclosure provide advantages over conventional systems and methods for determining nominal stresses insofar as hand calculations are not required, particular geometries of the structural components 12 are not required in the FE representation used by the FE analysis algorithms 22, mesh density used by the FE analysis algorithms 22 has little effect on estimated nominal stresses, and identification of specific geometric parameters, such as plate thickness, are not required for extrapolation of the nominal stresses. In addition, as described in greater detail herein, nominal stresses in non-welded structural components 12 that have stress raisers 36 due to geometric features, load applications, or other features, may also be estimated in a similar fashion as welded structural components 12.

While only certain features of the disclosure have been illustrated and described herein, many modifications and changes will occur to those skilled in the art. It is, therefore, to be understood that the appended claims are intended to cover all such modifications and changes as fall within the true spirit of the present disclosure. The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. § 112(f). However, for any claims containing elements designated in any other manner, it is intended that such elements are not to be interpreted under 35 U.S.C. § 112(f).

The invention claimed is:

1. A welding system comprising:
a welding control system, comprising:
memory media storing processor-executable instructions comprising finite element (FE) analysis algorithms configured to calculate stresses of a welded structural component and control a welding process of the welding system based at least in part on the calculated stresses; and
one or more processors configured to execute the FE analysis algorithms, wherein the FE analysis algorithms, when executed by the one or more processors:
calculate the stresses at a plurality of points from a base point along a base line of the welded structural component;
identify two or more points of the plurality of points by evaluating second derivatives of the calculated stresses for adjacent points of the plurality of points, wherein identifying the two or more points of the plurality of points comprises identifying each point of the two or more points of the plurality of points by identifying a subset of points adjacent the respective point, and wherein a second derivative of each of the subset of points is within a threshold percentage of each other;

estimate a nominal stress at the base point by extrapolating calculated stresses of the identified two or more points of the plurality of points to the base point;

output a control signal to adjust a welding process variable of the welding system for the manufacture of a subsequent welded structural component by the welding system based at least in part on the estimated nominal stress at the base point; and initiate the manufacture of the subsequent welded structural component using the welding system in accordance with the adjusted welding process variable of the welding system.

2. The welding system of claim 1, wherein the FE analysis algorithms, when executed by the one or more processors, spline-fit the calculated stresses versus the plurality of points from the base point along the base line of the welded structural component prior to identifying the two or more points.

3. The welding system of claim 1, wherein the one or more processors are configured to execute the FE analysis algorithms based at least in part on one or more models of the welded structural component.

4. The welding system of claim 1, wherein the FE analysis algorithms are not dependent upon a weld bead geometry of the welded structural component.

5. The welding system of claim 1, wherein the FE analysis algorithms are not significantly affected by a specific mesh density of the FE analysis algorithms.

6. The welding system of claim 1, wherein the welded structural component comprises a weld joint root at the base point.

7. The welding system of claim 1, wherein the subset of points comprises five points.

8. The welding system of claim 1, wherein the threshold percentage is 5%.

9. A welding system comprising:
a welding control system, comprising:
memory media storing processor-executable instructions comprising finite element (FE) analysis algorithms configured to calculate stresses of a welded structural component and control a welding process of the welding system based at least in part on the calculated stresses; and
one or more processors configured to execute the FE analysis algorithms, wherein the FE analysis algorithms, when executed by the one or more processors:
calculate the stresses at a plurality of points from a base point along a base line of the welded structural component;
spline-fit the calculated stresses versus the plurality of points from the base point along the base line of the welded structural component;
identify two or more points of the plurality of points by evaluating second derivatives of the spline-fitted calculated stresses for adjacent points of the plurality of points, wherein identifying the two or more points of the plurality of points comprises identifying each point of the two or more points of the plurality of points by identifying a subset of points adjacent the respective point, and wherein a second derivative of each of the subset of points is within a threshold percentage of each other;

estimate a nominal stress at the base point by extrapolating calculated stresses of the identified two or more points of the plurality of points to the base point;

output a control signal to adjust a welding process variable of the welding system for the manufacture of a subsequent welded structural component by the welding system based at least in part on the estimated nominal stress at the base point; and initiate the manufacture of the subsequent welded structural component using the welding system in accordance with the adjusted welding process variable of the welding system.

10. The welding system of claim 9, wherein the one or more processors are configured to execute the FE analysis algorithms based at least in part on one or more models of the welded structural component.

11. The welding system of claim 9, wherein the FE analysis algorithms are not dependent upon a weld bead geometry of the welded structural component.

12. The welding system of claim 9, wherein the FE analysis algorithms are not significantly affected by a specific mesh density of the FE analysis algorithms.

13. The welding system of claim 9, wherein the welded structural component comprises a weld joint root at the base point.

14. The welding system of claim 9, wherein the subset of points comprises five points.

15. The welding system of claim 9, wherein the threshold percentage is 5%.

16. A welding control system comprising:
memory media storing processor-executable instructions comprising finite element (FE) analysis algorithms configured to calculate stresses of a welded structural component and control a welding process of a welding system based at least in part on the calculated stresses; and
one or more processors configured to execute the FE analysis algorithms, wherein the FE analysis algorithms, when executed by the one or more processors, cause the welding control system to:
calculate the stresses at a plurality of points from a base point along a base line of the welded structural component;
spline-fit the calculated stresses versus the plurality of points from the base point along the base line of the welded structural component;
identify two or more points of the plurality of points by evaluating second derivatives of the spline-fitted calculated stresses for adjacent points of the plurality of points, wherein identifying the two or more points of the plurality of points comprises identifying each point of the two or more points of the plurality of points by identifying a subset of points adjacent the respective point, wherein a second derivative of each of the subset of points is within a threshold percentage of each other, wherein the threshold percentage is 5%, and wherein the subset of points comprises five points;
estimate a nominal stress at the base point by extrapolating calculated stresses of the identified two or more points of the plurality of points to the base point; and
output a control signal to adjust a welding process variable of the welding system for the manufacture of a subsequent welded structural component by the welding system based at least in part on the estimated nominal stress at the base point; and initiate the manufacture of the subsequent welded structural component using the welding system in accordance with the adjusted welding process variable of the welding system.

17. The welding control system of claim 16, wherein the one or more processors are configured to execute the FE analysis algorithms based at least in part on one or more models of the welded structural component.

18. The welding control system of claim 16, wherein the FE analysis algorithms are not dependent upon a weld bead geometry of the welded structural component.

19. The welding control system of claim 16, wherein the FE analysis algorithms are not significantly affected by a specific mesh density of the FE analysis algorithms.

20. The welding control system of claim 16, wherein the welded structural component comprises a weld joint root at the base point.

* * * * *